(12) United States Patent
Sun et al.

(10) Patent No.: US 6,603,013 B2
(45) Date of Patent: Aug. 5, 2003

(54) HETEROGENEOUSLY CATALYZED PROCESS FOR CROSS COUPLING ALKENYL HALIDES WITH BORONIC ACIDS

(75) Inventors: Yongkui Sun, Bridgewater, NJ (US); Carl LeBlond, Somerset, NJ (US); John R. Sowa, Jr., Morristown, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/906,247

(22) Filed: Jul. 16, 2001

(65) Prior Publication Data

US 2002/0045775 A1 Apr. 18, 2002

Related U.S. Application Data

(60) Provisional application No. 60/218,989, filed on Jul. 17, 2000.

(51) Int. Cl.[7] .................... C07C 1/32; C07C 17/269; C07C 51/353; C07C 201/12; C07D 213/127
(52) U.S. Cl. .............. 546/352; 548/134; 548/136; 548/202; 548/235; 548/560; 548/585; 548/438
(58) Field of Search .............. 546/352; 548/134, 548/136, 202, 235, 560; 585/438

(56) References Cited

U.S. PATENT DOCUMENTS 5,744,635 A * 4/1998 Brayer et al. ............... 546/341

OTHER PUBLICATIONS

Patterson, A.M. et al, "The Ring Index, 2nd Ed.", American Chemical Society, COlumbus, OH, 1960, pp. 30–31.*
Genet, J.P. et al, Synlett, 1992, 715–717.*
Synlett, 1996, 356–358.*
LeBlond, Carl R., et al.; "Activation of Aryl Chlorides for Suzuki Cross–Coupling by Ligandless, Heterogeneous Palladium"; Organic Letters; vol. 3(10); pp. 1555–1557; 2001.
Marck, G., et al., Tetrahedron Letters, vol. 35, pp. 3277–3280, 1994.
Gala, D., et al., M. Org. Proc. Res. Dev., vol. 1, pp. 163–164, 1997.
Xiaohong Bei, et al., Tetrahedron Letters, vol. 40, pp. 3855–3858, 1999.
Chunming Zhang, et al., J. Org. Chem., vol. 64, pp. 3804–3805, 1999.
John P. Wolfe, et al., J. Am. Chem. Soc., vol. 121, pp. 9550–9561, 1999.
Adam F. Littke, et al., Angew. Chem. Int. Ed., vol. 37, pp. 3387–3388, 1998.
Abstract of JP2000336045, Goto, Yasuyuki, et al., Method For Preparation of Biaryl Derivatives By Coupling Reaction On Arylboronic Acids, 2000.

* cited by examiner

*Primary Examiner*—Richard L. Raymond
*Assistant Examiner*—Thomas McKenzie
(74) *Attorney, Agent, or Firm*—Richard S. Parr; Valerie J. Camara; Mark R. Daniel

(57) ABSTRACT

The present invention relates to a process wherein heterogeneous finely-dispersed palladium catalysts are used in a cross-coupling reaction of alkenyl halides and aryl or heteroaryl boronic acids in the presence of base in an aprotic solvent to produce aryl- or heteroaryl-olefin compounds of Formula I:

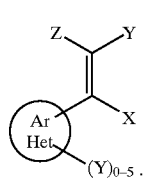

15 Claims, No Drawings

HETEROGENEOUSLY CATALYZED PROCESS FOR CROSS COUPLING ALKENYL HALIDES WITH BORONIC ACIDS

This application claims the benefit of U.S. Provisional Application No. 60/218,989, filed Jul. 17, 2000.

BACKGROUND OF THE INVENTION

The Suzuki cross-coupling of organic electrophiles with boronic acid and boronates esters constitutes the most direct and efficient approach for the formation of carbon—carbon bonds. Generally $C(sp^3)$, $C(sp^2)$ and $C(sp)$ boronic acids and boronate esters have been successfully employed as nucleophiles. While $C(sp^2)$ and $C(sp)$ have been successfully used as the electrophilic partner, only few cases of $C(sp^3)$ electrophiles have been demonstrated. Homogeneous Pd catalysts such as $Pd(dppf)_2$ or $Pd(PPh_3)_4$ are typically used for these Suzuki cross-couplings See N. Miyaura, et al., *Chem. Rev.* 1995, 95, 2457–2483; P. L. Castle et al., *Tetrahedron Lett.* 1986, 27, 6013; T. Ishiyama et al., *Chem. Lett.* 1992, 691; A. B. Charette et al., *Tetrahedron Lett.* 1997, 38, 2809–2812; N. Miyaura et al., *J. Am. Chem. Soc.* 1989, 111, 314; T. Ishiyama et al., *Synlett* 1991, 687.

This invention relates to a process wherein heterogeneous, finely dispersed Pd catalysts are used to activate alkenyl halides for cross coupling with boronic acids. The process provides for use with either electron-withdrawing or electron-donating substituents for cross coupling with boronic acids. Unlike homogeneous catalysis, the heterogeneously catalyzed Suzuki cross-coupling process provides several advantages, such as ease of product separation and recycling of the catalysts, which provide an overall simplified and cost-effective process. It also eliminate the side reactions that may occur between aryl groups of aryl phosphines (ligand) and the boronic acid. See M. G. Villeger, et al., *Tetrahedron Lett.* 1994, 35, 3277–3280; Gala, D., et al *Org. Proc. Res. Dev.* 1997, 1, 163–164; V. V. Bykov, et al, *Russian Chemical Bulletin* 1997, 46, 1344 and David S. Ennis, et al, *Org. Proc. Res. Dev.* 1999, 3, 248.

SUMMARY OF THE INVENTION

The present invention is directed to a process for a carbon—carbon coupling reaction by using palladium heterogeneous catalysis to activate alkenyl halides for cross coupling with boronic acid to prepare a compound of formula I,

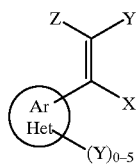
I comprising reacting a boronic acid of formula II,

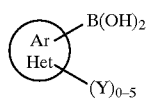
II with an alkenyl halide of formula III,

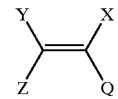
III wherein X, Y and Z are independently hydrogen, $CF_3$, $C_{1-6}$ alkoxy, $NO_2$, CN, halo, $C_{1-6}$alkyl, $NH_2$, COOH, $COO(C_{1-6}$ alkyl), or $N[(C_{1-6}$ alkyl$]_2$, acetanilide, amide, $C_{2-6}$ alkenyl, or aryl; and Q is F, Cl, Br, or I;

in the presence of a heterogeneous palladium catalyst and a base in an aprotic solvent to produce a compound of formula I.

DETAILED DESCRIPTION OF THE INVENTION

The present invention relates to a process for a carbon—carbon coupling reaction by using palladium heterogeneous catalysis to activate alkenyl halides for cross coupling with boronic acid to produce the carbon—carbon coupled compound containing aryl, heteroaryl, and alkenyl moieties.

The present invention is related to a process for synthesizing a compound of formula I:

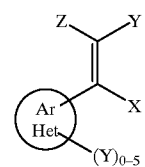
I comprising reacting a boronic acid of formula II,

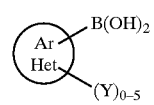
II with an alkenyl halide of formula III:

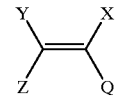
III wherein X, Y and Z are independently hydrogen, $CF_3$, $C_{1-6}$ alkoxy, $NO_2$, CN, halo, $C_{1-6}$ alkyl, $NH_2$, COOH, $COO(C_{1-6}$ alkyl), or $N[(C_{1-6}$ alkyl$]_2$, acetanilide, amide, $C_{2-6}$ alkenyl, or aryl; and Q is F, Cl, Br, or I; in the presence of a heterogeneous palladium catalyst and a base in an aprotic solvent to produce a compound of formula I.

The process as recited above, wherein the alkenyl halide is selected from the group consisting of α-bromostyrene, 1-bromo-2-methylpropene, α-chlorostyrene, 1-chloro-2-methylpropene, α-iodostyrene, and 1-iodo-2-methylpropene.

The process as recited above, wherein and the boronic acid is selected from the group consisting of phenyl boronic acid, 2-phenylvinylboronic acid, and phenylethenylboronic acid.

The process as recited above, wherein the heterogeneous palladium catalyst is finely dispersed palladium on a solid support.

The process as recited above, wherein the solid support is selected from the group consisting of carbon (Pd/C), silica, alumina, titania, and mesopourous zeolitic materials.

The process as recited above, wherein the heterogeneous palladium catalyst is finely dispersed palladium without a solid support.

The process as recited above, wherein the finely dispersed palladium is finely dispersed palladium metal (Pd Black) or finely dispersed palladium generated from homogeneous palladium acetate.

The process as recited above, wherein the heterogeneous palladium catalyst is finely dispersed palladium (colloidal) stabilized by organic polymers.

The process as recited above, wherein the aprotic solvent selected from the group consisting of N,N-dimethylacetamide (DMA), N,N-dimethylformamide (DMF), N-methylpyrrolidinone (NMP), dioxane, ethylene glycol dimethyl ether (DME), diethoxymethane (DEM), tetrahydrofuran (THF) or a combination of one or more of the above with water is added.

The process as recited above, wherein the solvent is NMP or DMA in combination with water.

The process as recited above, wherein a ratio of solvent to water is about 30:0.5 to about 5:0.5, preferably from about 25:1 to about 5:1, and most preferably from about 20:1 to about 10:1.

The process as recited above, wherein the base is selected from the group consisting of triethylamine, trimethylamine, ethyldimethylamine, tri-n-propylamine, 1,8-diazabicyclo[5.4.0.]undec-7-ene (DBU), pyridine, lutidine, collidine, 4-dimethylaminomethyl-pyridine, sodium carbonate, sodium bicarbonate, potassium bicarbonate, potassium carbonate, potassium sodium tartrate, potassium tartrate, potassium bitartrate, sodium tartrate, and sodium bitartrate. The preferred base is pyridine, potassium sodium tartrate, sodium carbonate, sodium bicarbonate, potassium bicarbonate, or potassium carbonate.

The present invention is described herein in detail using the terms defined below unless otherwise specified.

As used herein, the term "alkyl" refers, unless otherwise indicated, includes those alkyl groups of designated number of carbon atoms of either a straight, branched or cyclic configuration. Preferred alkyl groups include methyl, ethyl, propyl, isopropyl, butyl, t-butyl, cyclopentyl and cyclohexyl and the like.

The term "alkenyl" refers to a hydrocarbon radical straight, branched or cyclic containing a specified number of carbon atoms and at least one unsaturation. Preferred alkenyl groups include ethenyl, propenyl, butenyl, cyclohexenyl and the like.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted with substituents selected from the group consisting of $CF_3$, $C_{1-6}$ alkoxy, $NO_2$, CN, halo, $C_{1-6}$ alkyl, $NH_2$, $N[(C_{1-6}$ alkyl)]$_2$, acetanilide, amide, COOH and COO($C_{1-6}$ alkyl), and $C_{2-6}$alkenyl. Preferred aryls are phenyl and naphthyl.

The term "heteroaryl" refers to a monocyclic aromatic hydrocarbon group having 5 or 6 ring atoms, or a bicyclic aromatic group having 8 to 10 atoms containing at least one heteroatom selected from O, S or N, in which a carbon or nitrogen atom is the point of attachment, and in which one or two additional carbon atoms is optionally replaced by a heteroatom selected from 0 or 5, and in which from 1 to 3 additional carbon atoms are optionally replaced by nitrogen heteroatoms, the heteroaryl group being optionally substituted as recited above in aryl group. Examples of heteroaryl are pyrrole, pyridine, oxazole, and thiazole. Additional nitrogen atoms may be present together with the first nitrogen and oxygen or sulfur, giving, e.g., thiadiazole.

represents aryl or heteroaryl group as defined above, and aryl or heteroaryl may be optionally substituted with substituents as recited above.

X, Y and Z substituents are suitable electron-withdrawing or electron-donating group, such as hydrogen, $CF_3$, $C_{1-6}$ alkoxy, $NO_2$, CN, halo, $C_{1-6}$ alkyl, $NH_2$, COOH and COO($C_{1-6}$ alkyl), $N[(C_{1-6}$alkyl)]$_2$, acetanilide, amide, $C_{6-10}$ aryl and the like, provided that X cannot be $CF_3SO_3$ or iodo and bromo when it is halo. Preferred substituents are $CF_3$, $C(O)C_{1-6}$ alkyl, $NO_2$, and CN, OH, $C_{1-6}$ alkyl and $C_{1-6}$ alkoxy.

The term "heteroatom" means O, S or N, selected on an independent basis.

Halogen, halide and "halo" refer to bromine, chlorine, fluorine and iodine.

Suitable bases for the present invention include trialkylamines such as triethylamine, trimethylamine, ethyldimethylamine, tri-n-propylamine and the like, 1,8-diazabicyclo[5.4.0.]undec-7-ene (DBU), pyridine, lutidine, collidine, 4-dimethylaminomethyl-pyridine, sodium methoxide, potassium methoxide, sodium ter-butoxide, potassium tert-butoxide, inorganic carbonates and bicarbonates such as sodium carbonate, sodium bicarbonate, potassium bicarbonate, potassium carbonate, and the like and tartrates such as potassium sodium tartrate, potassium tartrate, potassium bitartrate, sodium tartrate, sodium bitartrate and the like. Preferred bases are pyridine, potassium sodium tartrate, sodium carbonate, sodium bicarbonate, potassium bicarbonate, or potassium carbonate. The more preferred base is potassium carbonate.

Suitable heterogeneous catalyst are those which contain a palladium (Pd) source including those that are finely dispersed palladium with or without a solid support; or finely dispersed palladium stabilized by organic polymers such as poly(vinylpyrrolidinones), poly(vinyl alcohol) and poly(methyl vinyl ether).

In the case of finely dispersed palladium on a solid support, this includes palladium supported on carbon (Pd/C), silica, alumina, titania, and mesopourous or zeolitic materials. The state of the palladium can be in a reduced or non-reduced form in which case it can be reduced in situ with any suitable reducing agents including aryl boronic acids, potassium or sodium formate, hydrogen, borohydride reagents, silanes, aluminum hydride reagents, hydrazine and the like. In the case of finely dispersed palladium without a solid support this includes finely dispersed palladium metal (Pd Black) and finely dispersed palladium generated from homogeneous palladium sources (such as palladium acetate) by action of a suitable reducing agent including potassium or sodium formate, hydrogen, borohydride reagents, silanes, aluminum hydride reagents, hydrazine and the like. In the case of finely dispersed palladium stabilized by organic polymers, this includes colloidal palladium stabilized by organic polymers such as poly(vinylpyrrolidinones), poly(vinyl alcohol) and poly (methyl vinyl ether).

The reaction is generally carried out using an aprotic solvent such as N,N-dimethylacetamide (DMA), N,N-dimethylformamide (DMF), N-methylpyrrolidinone (NMP), dioxane, ethylene glycol dimethyl ether (DME), diethoxymethane (DEM), tetrahydrofuran (THF), $C_{1-6}$ alcohol such as methanol, propanol and ethanol, benzene and the like or an appropriate combination of one or more of the above solvent with water. Preferable solvents are NMP or DMA in combination with water. When solvent is combined with water, the ratio of solvent to water is in the range of about 30:0.5 to about 5:0.5, preferably from about 25:1 to about 5:1 and most preferably from about 20:1 to about 10:1.

The process of the present invention is illustrated by the following generic reaction scheme:

Reaction Scheme A

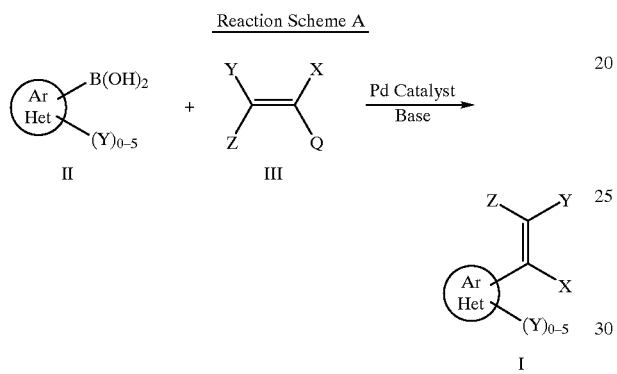

As shown in Reaction Scheme A, the compounds used in the synthesis of the compounds of the present invention have, in some cases, been described in the chemical literature. One skilled in the art can adapt a previously published synthesis of an analogous compound to prepare the requisite compound in a straightforward manner without undue experimentation.

In general, the cross coupling reaction can be accomplished by reacting alkenyl halide (III) with aryl or heteroaryl boronic acid (II) in the presence of a heterogeneous palladium catalyst and a base in an aprotic solvent such as N,N-dimethylacetamide (DMA), N,N-dimethylformamide (DMF), N-methylpyrrolidinone (NMP), dioxane and the like or a combination of the above with water, preferably NMP or DMA in combination with water to give a final compound of formula I. Suitable bases are inorganic carbonates and bicarbonates such as sodium carbonate, sodium bicarbonate, potassium bicarbonate, potassium carbonate and the like, and tartrates such as potassium sodium tartrate, potassium tartrate, potassium bitartrate, sodium tartrate, sodium bitartrate and the like, preferably potassium carbonate. Reaction is generally carried out in the presence of a heterogeneous palladium catalyst such as Pd/C at a temperature range of about 35° C. to about 120° C., preferably about 50° C. to about 100° C., and most preferably about 75° C. to about 85° C., followed by an appropriate work-up and isolation procedure familiar to those skilled in the art to yield the final compound of formula I. When solvent is combined with water, the ratio of solvent to water is in the range of about 30:0.5 to about 5:0.5, preferably from about 25:1 to about 5:1, more preferably from about 20:1 to about 10:1, and most preferably about 20:1.

The preferable palladium catalyst system is one with an optimal palladium level of about 0.1 mole % to about 15 mole %, more preferably about 3 mole % to about 10 mole %.

The final product may be characterized structurally by standard techniques such as NMR, IR, MS, and UV. For ease of handling, the final product, if not crystalline, may be lyophilized from water to afford an amorphous, easily handled solid.

The compounds of the present invention are valuable tools for the synthesis of drug intermediates, for example antibacterial agents.

The invention is further described in connection with the following non-limiting example.

EXAMPLE 1

Cross-coupling of α-bromostyrene with Phenylboronic Acid

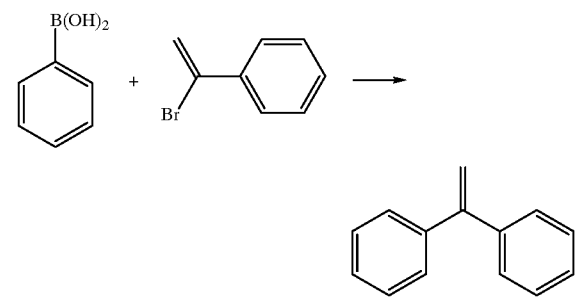

To a clean 40 ml schlenk tube is added about 85 mg (5 mol % Pd based on α-bromostyrene) of 5 wt % Pd on carbon (PMC type 1610 C, 1.72% water), about 119 mg phenylboronic acid (0.96 mmol), about 221 mg $K_2CO_3$ (1.6 mmol), 5 ml of N-methylpyrrolidinone and 1 ml of distilled water. A magnetic stir bar is added, and then the schlenk tube is sealed with a rubber septum and inerted with four vacuum/argon purge cycles. The α-bromostyrene (0.8 mmol, 148.7 mg) is added, and the schlenk tube is inerted with four vacuum/argon cycles placed in an oil bath at about 80° C. and stirred for about 24 hours. The reaction mixture is then filtered and the catalyst cake is washed with pentane. The organic layer is washed with 2M NaOH, dried with $MgSO_4$ and distilled to a white solid (yield about 94%).

What is claimed is:

1. A process for synthesizing a compound of formula I,

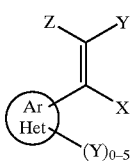

comprising reacting a boronic acid of formula II,

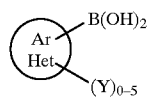

with an alkenyl halide of formula III,

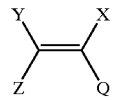

wherein X, Y and Z are independently hydrogen, $CF_3$, $C_{1-6}$ alkoxy, $NO_2$, CN, halo, $C_{1-6}$ alkyl, $NH_2$, COOH, COO($C_{1-6}$ alkyl), or $N[(C_{1-6}\ alkyl)]_2$, acetanilide, amide, $C_{2-6}$ alkenyl, or aryl; and Q is Cl, Br, or I;
in the presence of a heterogeneous palladium catalyst and a base in an aprotic solvent to produce a compound of formula I.

2. The process of claim 1, wherein the alkenyl halide is selected from the group consisting of α-bromostyrene, 1-bromo-2-methylpropene, α-chlorostyrene, 1-chloro-2-methylpropene, α-iodostyrene, and 1-iodo-2-methylpropene.

3. The process of claim 2, wherein the boronic acid is phenyl boronic acid.

4. The process of claim 3, wherein the heterogeneous palladium catalyst is finely dispersed palladium on a solid support.

5. The process of claim 4, wherein the solid support is selected from the group consisting of carbon (Pd/C), silica, alumina, titania, and mesopourous zeolitic materials.

6. The process of claim 1, wherein the heterogeneous palladium catalyst is finely dispersed palladium without a solid support.

7. The process of claim 6, wherein the finely dispersed palladium is finely dispersed palladium metal (Pd Black) or finely dispersed palladium generated from homogeneous palladium acetate.

8. The process of claim 1, wherein the heterogeneous palladium catalyst is finely dispersed palladium (colloidal) stabilized by organic polymers.

9. The process of claim 1, wherein the aprotic solvent selected from the group consisting of N,N-dimethylacetamide (DMA), N,N-dimethylformamide (DMF), N-methylpyrrolidinone (NMP), dioxane, ethylene glycol dimethyl ether (DME), diethoxymethane (DEM), tetrahydrofuran (THF) or a combination of one or more of the above with water is added.

10. The process of claim 9, wherein the aprotic solvent is NMP or DMA in combination with water.

11. The process of claim 10, wherein a ratio of aprotic solvent to water is about 30:0.5 to about 5:0.5.

12. The process of claim 11, wherein the ratio of aprotic solvent to water is from about 25:1 to about 5:1.

13. The process of claim 12, wherein the ratio of aprotic solvent to water is from about 20:1 to about 10:1.

14. The process of claim 1, wherein the base is selected from the group consisting of triethylamine, trimethylamine, ethyldimethylamine, tri-n-propylamine, 1,8-diazabicyclo[5.4.0.]undec-7-ene (DBU), pyridine, lutidine, collidine, 4-dimethylaminomethyl-pyridine, sodium carbonate, sodium bicarbonate, potassium bicarbonate, potassium carbonate, potassium sodium tartrate, potassium tartrate, potassium bitartrate, sodium tartrate, and sodium bitartrate.

15. The process of claim 14, wherein the base is pyridine, potassium sodium tartrate, sodium carbonate, sodium bicarbonate, potassium bicarbonate, or potassium carbonate.

* * * * *